(12) United States Patent
Billotte

(10) Patent No.: US 6,713,461 B1
(45) Date of Patent: Mar. 30, 2004

(54) PHARMACEUTICAL COMPLEX

(75) Inventor: Anne Billotte, County of Kent (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/606,508

(22) Filed: Jun. 29, 2000

(30) Foreign Application Priority Data

Jun. 29, 1999 (GB) .............................. 9915231

(51) Int. Cl.⁷ ........................ A01N 43/04; A01N 61/00; C07H 1/00
(52) U.S. Cl. ............... 514/58; 514/1; 514/23; 514/25; 514/946; 536/1.11
(58) Field of Search ............... 514/1, 23, 25, 514/946, 58; 536/1.11

(56) References Cited

FOREIGN PATENT DOCUMENTS

| WO | WO 9802186 | 1/1988 |
|---|---|---|
| WO | WO 9111172 | 8/1991 |
| WO | WO 91/14680 | 10/1991 |
| WO | 9114681 | 10/1991 |
| WO | WO 9206973 | 4/1992 |
| WO | WO 9402518 | 2/1994 |
| WO | 9420091 | 9/1994 |
| WO | 9524221 | 9/1995 |
| WO | WO 9606842 | 3/1996 |
| WO | WO 9827089 | 6/1998 |
| WO | WO 9839327 | 9/1998 |
| WO | WO 9901135 | 1/1999 |
| WO | WO 99/01135 | * 1/1999 |
| WO | WO 0006161 | 2/2000 |

* cited by examiner

Primary Examiner—Jezia Riley
(74) Attorney, Agent, or Firm—David R. Kurlandsky; Richard L. Catania; Kristine L. Konstas

(57) ABSTRACT

This invention relates to a complex of eletriptan and a sulphobutylether-beta-cyclodextrin, or a pharmaceutically acceptable salt thereof, and to processes for the preparation of, pharmaceutical formulations including, and the uses of, such a complex.

27 Claims, No Drawings

PHARMACEUTICAL COMPLEX

This invention relates to a complex of eletriptan and a sulphobutylether-beta-cyclodextrin, or a pharmaceutically acceptable salt thereof, and to processes for the preparation of, pharmaceutical formulations including, and the uses of, such a complex.

Eletriptan, 3-([1-methylpyrrolidin-2(R)-yl]methyl)-5-(2-phenylsulphonylethyl)-1H-indole, is disclosed in WO-A-92/06973. A preferred hydrobromide salt form of eletriptan is disclosed in WO-A-96/06842. WO-A-99/01135 discloses a pharmaceutical formulation comprising eletriptan hemisulphate and caffeine. WO-A-00/06161 describes the use of eletriptan for the prevention of migraine recurrence.

Eletriptan is a $5HT_{1B/1D}$ receptor agonist and has been shown to be highly effective for the treatment of migraine and the prevention of migraine recurrence. Eletriptan has also been disclosed for the treatment of hypertension, emesis, depression, anxiety, an eating disorder, obesity, drug abuse, cluster headache, pain, chronic paroxysmal hemicrania and a headache associated with a vascular disorder.

In order to administer eletriptan, or a salt thereof, by the intranasal route, it is desirable that a formulation does not produce unacceptable levels of effect, such as irritancy, on the nasal mucosae. It has been found that the formulations described in WO-A-99/01135 comprising eletriptan hemisulphate and caffeine are irritant on the nasal mucosae.

Accordingly, it is an object of the present invention to provide a well-tolerated pharmaceutical formulation of eletriptan, or a salt thereof, that is suitable for administration by the intranasal route.

It is further object of this invention to provide a well-tolerated, stable, aqueous, pharmaceutical formulation containing eletriptan, or a salt thereof, that is suitable for parenteral, preferably, intranasal administration and which enables the drug to have good bioavailability and rapid onset of action.

WO-A-91/11172 and WO-A-94/02518 disclose sulphoalkyl ether cyclodextrin derivatives.

WO-A-98/02186 discloses an inclusion complex of (a) an indole selective serotonin ($5-HT_{1D}$) agonist or a pharmaceutically acceptable salt thereof and (b) an unsubstituted or substituted beta- or gamma-cyclodextrin, together with pharmaceutical compositions thereof.

It has now been found that eletriptan, or a salt thereof, can form a complex with certain sulphobutylether-beta-cyclodextrin derivatives of the type disclosed in WO-A-91/11172. Although this complexation undesirably and unpredictably decreases the aqueous solubility of eletriptan, or a salt thereof, it unexpectedly and advantageously provides a complex which is well-tolerated when administered intranasally, principally since it has a negligible irritant effect on the nasal mucosae in comparison with both the known caffeine formulations of eletriptan disclosed in WO-A-99/01135 and other cyclodextrin complexes of eletriptan.

Accordingly, the present invention provides a complex of eletriptan and a cyclodextrin derivative of the formula (I):

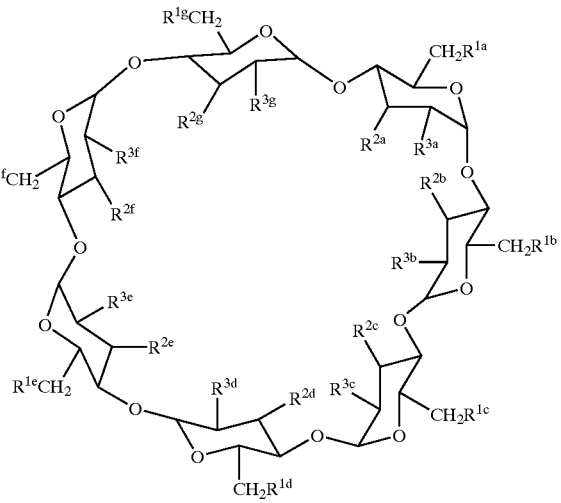

(I)

wherein
$R^{1a-g}$, and $R^{3a-g}$ each independently represent —OH or —O(CH$_2$)$_4$SO$_3$H; provided that at least one of $R^{1a-g}$ represents —O(CH$_2$)$_4$SO$_3$H: or a pharmaceutically acceptable salt thereof.

Pharmaceutically acceptable salts of particular interest associated with the eletriptan component are acid addition and base salts thereof. Suitable acid addition salts are formed from acids which form non-toxic salts and examples are the hydrochloride, hydrobromide, hydroiodide, sulphate, bisulphate, nitrate, phosphate, hydrogen phosphate, acetate, maleate, fumarate, lactate, tartrate, citrate, gluconate, succinate, saccharate, benzoate, methanesulphonate, ethanesulphonate, benzenesulphonate, p-toluenesulphonate and pamoate salts. Hydrobromide and sulphate, including hemisulphate, salts are preferred. Suitable base salts are formed from bases which form non-toxic salts and examples are the sodium, potassium, aluminium, calcium, magnesium, zinc and diethanolamine salts.

Pharmaceutically acceptable salts of particular interest associated with the cyclodextrin ring component are base salts of the —O(CH$_2$)$_4$SO$_3$H groups, for example, alkali metal salts, such as sodium salts.

For a review on suitable salts see Berge et al, J. Pharm. Sci., 66, 1–19, 1977.

A pharmaceutically acceptable salt may readily be prepared by mixing together solutions of eletriptan, the cyclodextrin or the complex, and the desired acid or base, as appropriate. The salt may precipitate from solution and be collected by filtration or may be recovered by evaporation of the solvent. When a salt of eletriptan and/or the cyclodextrin are/is separately prepared, these/this may then be used for the preparation of the complex.

A polymorph of eletriptan, or a salt thereof, may also be used for the purpose of the present invention.

Preferably, the average number of —O(CH$_2$)$_4$SO$_3$H groups per molecule of formula (I) is in the range of from 6.1 to 6.9, for example, 6.5 or about 6.5.

It is preferred that each —O(CH$_2$)$_4$SO$_3$H present is in the form of an alkali metal salt (such as the sodium salt).

Preferably, the molar ratio of eletriptan:cyclodextrin derivative of the formula (I) is from 1:1 to 15:1, most preferably from 1:1 to 10:1.

Preferably, eletriptan is present in the form of the hemisulphate salt.

The complex can be administered alone but will generally be administered in admixture with a pharmaceutically acceptable excipient, diluent or carrier selected with regard to the intended route of administration and standard pharmaceutical practice.

For example, the complex can be administered orally, buccally or sublingually in the form of tablets, capsules, ovules, elixirs, solutions or suspensions, which may contain flavouring or colouring agents, for immediate-, delayed-, sustained-, pulsed- or controlled-release applications.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or a high molecular weight polyethylene glycol. For aqueous suspensions and/or elixirs, the complex may be combined with various sweetening or flavouring agents, colouring matter or dyes, with emulsifying and/or suspending agents and with diluents such as water, ethanol, propylene glycol and glycerin, and combinations thereof.

The complex can also be administered parenterally, for example, intravenously, intraarterially, intraperitoneally, intrathecally, intraventricularly, intrasternally, intracranially, intramuscularly or subcutaneously, or it may be administered by infusion techniques. It is best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

For oral and parenteral administration to human patients, the daily dosage level of eletriptan will usually be from 0.001 to 0.50 mg/kg (in single or divided doses).

Thus tablets or capsules containing the complex may contain from 5 to 240 mg of eletriptan, or a salt thereof, for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

The complex can also be administered intranasally or by inhalation and is conveniently delivered as a single dose or multi-dose in the form of a dry powder inhaler or an aerosol spray presentation from a pressurised container, pump, atomiser, spray or nebuliser, with or without the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark]) or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, atomiser, spray or nebuliser may contain a solution or suspension of the complex, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of the complex and a suitable powder base such as lactose or starch.

Aerosol or dry powder formulations are preferably arranged so that each metered dose or "puff" contains from 1 to 16 mg of eletriptan for delivery to the patient.

Alternatively, the complex can be administered in the form of a suppository or pessary, or it may be applied topically in the form of a lotion, solution, cream, ointment or dusting powder. The complex may also be transdermally administered, for example, by the use of a skin patch.

For application topically to the skin, the complex can be formulated as a suitable ointment containing the complex suspended or dissolved in, for example, a mixture with one or more of the following: mineral oil, liquid petrolatum, white petrolatum, propylene glycol, polyoxyethylene polyoxypropylene compound, emulsifying wax and water. Alternatively, it can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The complex of the invention may be prepared from an aqueous solution or slurry of eletriptan, or a salt thereof, and the cyclodextrin, or a salt thereof, by conventional methods. Where a solid complex is required, the solution or slurry may be dried by spray-drying or freeze-drying (lyophilisation). Alternatively, eletriptan, or a salt thereof, and the cyclodextrin, or a salt thereof, can be mixed and the powder mixture moistened with water. The mixture may then be vigorously mixed to form a paste and dried at an elevated temperature, preferably under reduced pressure, to remove the water. The dried complex may be crushed and sieved to the desired particle size.

The solid complex can then be formulated for administration as a pharmaceutical formulation by standard methods, for example, if an aqueous formulation is required the complex may be dissolved with stirring in water. A further suitable excipient, diluent or carrier may be incorporated in the formulation at the blending or mixing step. Alternatively, a pharmaceutical formulation including the present complex may be prepared by mixing eletriptan, or a salt thereof, and the cyclodextrin, or a salt thereof, together with a suitable excipient, diluent or carrier directly.

The complex can also be administered together with a prokinetic (e.g. metoclopramide) or antiemetic agent.

It is to be appreciated that all references herein to treatment include curative, palliative and prophylactic treatment.

Preferably, the complex is administered as a pharmaceutical formulation, most preferably, as an aqueous solution formulation.

Preferably, the pharmaceutical formulation is formulated for parenteral administration, for example, intranasal administration.

Preferably, a pharmaceutical formulation, most preferably, an aqueous pharmaceutical formulation, comprises one or more of the following excipients, diluents or carriers:

(a) an anti-oxidant, for example, citric acid or ascorbic acid;
(b) a co-solvent, for example, ethanol, glycerol or a PEG200–400; and
(c) an organic polymer, for example, a water-soluble organic polymer such as carboxymethylcellulose, polyvinylpyrrolidone or hydroxypropylmethyl cellulose.

The presence of an anti-oxidant increases the stability of the formulation.

The presence of an organic polymer or co-solvent optimises the bioavailability and increases the absorption and the onset of action of eletriptan.

Preferably, the present invention provides a pharmaceutical formulation, preferably an aqueous pharmaceutical formulation, including from 10 to 150 mg/g of eletriptan or a salt thereof (preferably the hemisulphate), and from 10 to 30% weight/weight of the sulphobutylether-beta-cyclodextrin.

Preferably, up to and including 1% weight/weight of an anti-oxidant such as citric acid or ascorbic acid can be present.

Preferably, up to and including 30% weight/weight of a co-solvent such as ethanol, glycerol or a PEG200–400, preferably glycerol, can be present.

Preferably, up to and including 0.5% weight/weight of an organic polymer such as a water soluble polymer, for example carboxymethylcellulose, polyvinylpyrrolidone or hydroxypropylmethyl cellulose, preferably carboxymethylcellulose or polyvinylpyrrolidone, can be present.

Preferably, from 10 to 150 mg/g of eletriptan hemisulphate is present.

Preferably, from 20 to 110 mg/g of eletriptan hemisulphate is present.

Preferably, from 50 to 120 mg/g of eletriptan hemisulphate is present.

Preferably, from 10 to 30% weight/weight of the sulphobutylether-beta-cyclodextrin is present.

Preferably, from 15 to 25% weight/weight of the sulphobutylether-beta-cyclodextrin is present.

Preferably, from 0.10 to 1.0% weight/weight of ascorbic acid is present.

Preferably, from 0.25 to 0.80% weight/weight of ascorbic acid is present.

Preferably, from 0.30 to 0.60% weight/weight of ascorbic acid is present.

Preferably, from 5.0 to 30.0% weight/weight of glycerol is present.

Preferably, from 10.0 to 25.0% weight/weight of glycerol is present.

Preferably, from 10.0 to 20.0% weight/weight of glycerol is present.

Preferably, from 0.05 to 0.5% weight/weight of carboxymethylcellulose or polyvinylpyrrolidone is present.

Preferably, from 0.05 to 0.2%, most preferably, from 0.1 to 0.2%, weight/weight of carboxymethylcellulose or polyvinylpyrrolidone is present.

Preferably, an aqueous pharmaceutical formulation is adjusted to a pH of from 4.0 to 9.0.

Preferably, an aqueous pharmaceutical formulation is adjusted to a pH of from 4.0 to 7.0.

Preferably, an aqueous pharmaceutical formulation is adjusted to a pH of from 4.0 to 5.0.

The following Examples illustrate the preparation of aqueous pharmaceutical formulations including the complex of the present invention. The formulations were prepared by the addition of eletriptan hemisulphate, the sulphobutylether-beta-cyclodextrin, glycerol or polyvinyl pyrrolidone, and ascorbic acid, to water (sufficient quantity to represent 80% of the final volume of the required formulation). The mixture was stirred to dissolve the solids and the resulting solution adjusted to the required pH using 1M aqueous sodium hydroxide solution. Water was then added to achieve the final volume required. The sulphobutylether-beta-cyclodextrin used has an average sulphobutylether substitution of 6.5 per cyclodextrin molecule, and each sulphobutylether unit was present as its sodium salt.

EXAMPLE 1

A formulation suitable for intranasal administration is an aqueous formulation comprising:
  100 mg/g of eletriptan hemisulphate;
  20% weight/weight of the sulphobutylether-beta-cyclodextrin;
  15% weight/weight of glycerol; and
  0.5% weight/weight of ascorbic acid:
  with the formulation adjusted to from pH 4.0 to 5.0, preferably about pH 4.5, using aqueous sodium hydroxide solution.

EXAMPLE 2

A formulation suitable for intranasal administration is an aqueous formulation comprising:
  80 mg/g of eletriptan hemisulphate;
  20% weight/weight of the sulphobutylether-beta-cyclodextrin;
  0.15% weight/weight of polyvinylpyrrolidone; and
  0.5% weight/weight ascorbic acid:
  with the composition adjusted to from pH 4.0 to 5.0, preferably about pH 4.5, using aqueous sodium hydroxide solution.

EXAMPLE 3

A formulation suitable for intranasal administration is an aqueous formulation comprising:
  80 mg/g of eletriptan hemisulphate;
  20% weight/weight of the sulphobutylether-beta-cyclodextrin;
  20% weight/weight of glycerol; and
  0.7% weight/weight of ascorbic acid:
  with the formulation adjusted to from pH 4.0 to 5.0, preferably about pH 4.5, using aqueous sodium hydroxide solution.

EXAMPLE 4

A formulation suitable for intranasal administration is an aqueous formulation comprising:
  80 mg/g of eletriptan hemisulphate;
  20% weight/weight of the sulphobutylether-beta-cyclodextrin;
  0.10% weight/weight of polyvinylpyrrolidone; and
  0.7% weight/weight ascorbic acid;
  with the composition adjusted to from pH 4.0 to 5.0, preferably about pH 4.5, using aqueous sodium hydroxide solution.

Biological Activity

The complex of the present invention may be tested for irritant effects on the nasal mucosae by the following method.

Test solutions were prepared as follows:
(1) an aqueous solution containing 10% wt/wt hydroxypropyl-beta-cyclodextrin (containing an average number of hydroxypropyl groups per molecule of cyclodextrin of 0.6);
(2) an aqueous solution containing 17% wt/wt of the present sulphobutylether-beta-cyclodextrin;
(3) an aqueous solution containing 10% wt/wt hydroxypropyl-beta-cyclodextrin (containing an average number of hydroxypropyl groups per molecule of cyclodextrin of 0.6) and 50 mg/ml of eletriptan hemisulphate; and
(4) an aqueous solution containing 17% wt/wt of the present sulphobutylether-beta-cyclodextrin and 50 mg/ml of eletriptan hemisulphate.

All the above solutions were adjusted to pH 4.2+/−0.2.

Female Sprague-Dawley rats were used for the studies. The animals were about 7 weeks old with a mean body weight of 199 g. Each study was performed on a group of five rats.

A 20 microliter volume of the test solution was instilled into the left nostril of each rat in the study group. The rats in each group were treated once daily with the same test solution for 7 days. The rats in each study group were observed daily for mortality and clinical signs. They were weighed on study days −2, 1 and 7. On study day 8 the rats were sacrificed and macroscopic and histopathological examinations were carried out on the tissues of the respiratory tract only of each rat.

No deaths were recorded. The results showed that test solutions (1), (2) and (4) did not produce any lesions. Test solution (3) induced minimal to mild hyperplasia and metaplasia of the respiratory epithelium and luminal exudate. These findings were interpreted as signs of minimal to mild irritation of the nasal turbinates.

It was concluded that test solution (4), containing a complex of eletriptan hemisulphate and the present sulphobutylether-beta-cyclodextrin, was non-irritant on the nasal mucosae when administered by the intranasal route.

What is claimed is:

1. A complex of eletriptan and a cyclodextrin derivative of formula (I):

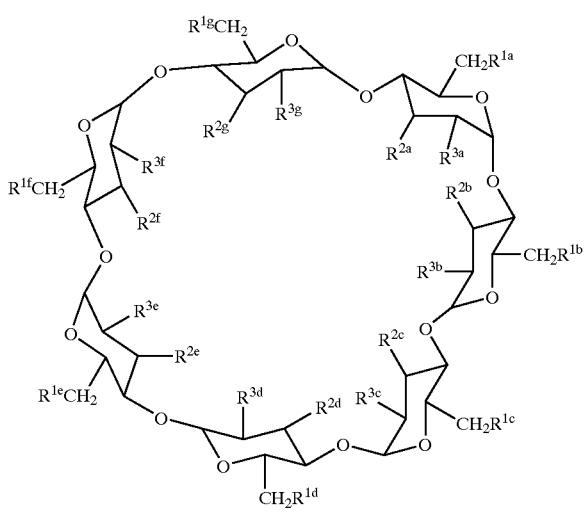

(I)

wherein
$R^{1a-g}$, $R^{2a-g}$ and $R^{3a-g}$ each independently represent —OH or —O(CH$_2$)$_4$SO$_3$H; provided that at least one of $R^{1a-g}$ represents —O(CH$_2$)$_4$SO$_3$H:
or a pharmaceutically acceptable salt thereof.

2. A complex according to claim 1, wherein the average number of —O(CH$_2$)$_4$SO$_3$H groups per molecule of the derivative of the formula (I) is in the range of from 6.1 to 6.9.

3. A complex according to claim 1 wherein each —O(CH$_2$)$_4$SO$_3$H group present in the derivative of the formula (I) is in the form of an alkali metal salt.

4. A complex according to claim 1 wherein the molar ratio of eletriptan:cyclodextrin derivative of the formula (I) is from 1:1 to 15:1.

5. A complex according to claim 4 wherein the molar ratio of eletriptan:cyclodextrin derivative of the formula (I) is from 1:1 to 10:1.

6. A complex according to claim 1 wherein eletriptan is present in the form of the hemisulphate salt.

7. A pharmaceutical formulation including a complex according to claim 1 and a pharmaceutically acceptable excipient, diluent or carrier.

8. A formulation according to claim 7 wherein from 50 to 120 mg/g of eletriptan hemisulphate is present.

9. A formulation according to claim 7 wherein from 15 to 25% weight/weight of the sulphobutylether-beta-cyclodextrin is present.

10. A formulation according to claim 7, including one or more of an anti-oxidant, a co-solvent and an organic polymer.

11. A formulation according to claim 10 wherein the anti-oxidant is ascorbic acid.

12. A formulation according to claim 11 wherein from 0.25 to 0.80% weight/weight of ascorbic acid is present.

13. A formulation according to claim 10 wherein the co-solvent is glycerol.

14. A formulation according to claim 13 wherein from 10.0 to 25.0% weight/weight of glycerol is present.

15. A formulation according to claim 10 wherein the organic polymer is carboxymethylcellulose or polyvinylpyrrolidone.

16. A formulation according to claim 15 wherein from 0.05 to 0.20% weight/weight of carboxymethylcellulose or polyvinylpyrrolidone is present.

17. A formulation according to claim 7 that is in the form of an aqueous solution.

18. An aqueous formulation according to claim 17 that has a pH of from 4.0 to 5.0.

19. A formulation according to claim 7 which is adapted for parenteral administration.

20. A formulation according to claim 7 which is adapted for intranasal administration.

21. A formulation according to claim 7 which is adapted for inhalation.

22. A formulation according to claim 7 that is an aqueous solution comprising:
80 mg/g of eletriptan hemisulphate;
20% weight/weight of the sulphobutylether-beta-cyclodextrin derivative of formula (I) having an average sulphobutylether substitution of 6.5 per cyclodextrin molecule with each sulphobutylether unit present as its sodium salt;
20% weight/weight of glycerol; and
0.7% weight/weight of ascorbic acid:
with the formulation having been adjusted to from pH 4.0 to 5.0, preferably about pH 4.5, using aqueous sodium hydroxide solution.

23. A formulation according to claim 7 that is an aqueous solution comprising:
80 mg/g of eletriptan hemisulphate;

20% weight/weight of the sulphobutylether-beta-cyclodextrin derivative of formula (I) having an average sulphobutylether substitution of 6.5 per cyclodextrin molecule with each sulphobutylether unit present as its sodium salt;

0.10% weight/weight of polyvinylpyrrolidone; and 0.7% weight/weight ascorbic acid:

with the composition having been adjusted to from pH 4.0 to 5.0, preferably about pH 4.5, using aqueous sodium hydroxide solution.

24. A method of treating in a mammal a disease for which a $5HT_{1B/1D}$ receptor agonist is indicated including treating said mammal with an effective amount of a complex according to claim 1.

25. A method of treating in a mammal migraine or preventing migraine recurrence in a mammal including treating said mammal with an effective amount of a complex according to claim 1.

26. A process for the preparation of a complex according to claim 1 which comprises combining eletriptan, or a pharmaceutically acceptable salt thereof, with the cyclodextrin derivative, or a pharmaceutically acceptable salt thereof.

27. A process for the preparation of a formulation according to claim 7 which comprises combining either (i) the complex comprising eletriptan and the cyclodextrin derivative of formula (I), or (ii) eletriptan, or a pharmaceutically acceptable salt thereof, and the cyclodextrin derivative, or a pharmaceutically acceptable salt thereof, with a pharmaceutically acceptable excipient, diluent or carrier.

* * * * *